United States Patent [19]
Baro et al.

[11] Patent Number: 5,082,941
[45] Date of Patent: Jan. 21, 1992

[54] PROCESS FOR PREPARING THE PIPERAZINE SALT OF 2,5-DIHYDROXYBENZENESULPHONIC ACID MONOTOSYLATE

[75] Inventors: Josep M. R. Baro, Esplugues de Llobregat; Salvador M. Giral, Terrassa; Josep M. F. Pons de Vall, Barcelona, all of Spain

[73] Assignee: Esteve Quimica S.A., Barcelona, Spain

[21] Appl. No.: 557,918

[22] Filed: Jul. 25, 1990

[30] Foreign Application Priority Data

Aug. 3, 1989 [ES] Spain .................................. 89 02754

[51] Int. Cl.$^5$ .................. C07D 295/00; C07C 303/32
[52] U.S. Cl. ................................. 544/358; 544/403; 544/410
[58] Field of Search .................. 544/410, 403, 358

[56] References Cited

U.S. PATENT DOCUMENTS 3,954,767  5/1976  Esteve-Subirana ................ 544/403
4,115,648  9/1978  Esteve-Subirana ................ 544/110

FOREIGN PATENT DOCUMENTS 99988    2/1984   European Pat. Off. .
2184654  12/1973  France .
2201888  5/1974   France .
2242975  4/1975   France .
2269931  12/1975  France .
414366   11/1979  Spain .

Primary Examiner—Cecilia Shen
Attorney, Agent, or Firm—Ladas & Parry

[57] ABSTRACT

The process is characterized in that the diethylamine salt or the ammonium salt of 2,5-dihydroxybenzenesulphonic acid is used as starting material, which salt is tosylated in an ammoniacal medium to lead in both cases to the production of the ammonium salt of 2,5-dihydroxybenzenesulphonic acid monotosylate, which in its turn is converted initially to the corresponding piperazine disalt which is separated in an aqueous medium, and finally in an aqueous-alcoholic medium the piperazine salt of 2,5-dihydroxybenzenesulphonic acid monotosylate, also known as piperazine sultosylate, is obtained.

Medicinal applications.

3 Claims, No Drawings

PROCESS FOR PREPARING THE PIPERAZINE SALT OF 2,5-DIHYDROXYBENZENESULPHONIC ACID MONOTOSYLATE

The present invention relates to a process for preparing the piperazine salt of 2,5-dihydroxybenzenesulphonic acid monotosylate, of formula I, a very pure white product being obtained. The compound of formula I, also known by the generic name of pipearizine sultosylate, is used as a hypocholesterolaemic, hypotriglycaemic and hypolipaemic agent.

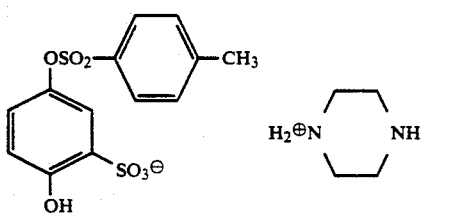

(I)

BACKGROUND OF THE INVENTION

Piperazine sultosylate appears specifically described in Certificate of Addition No. 477,098 (Lab. del Dr. Esteve, S. A.) of Spanish Patent No. 414,366 (Lab. del Dr. Esteve, S. A.). The product is obtained from the pyridine salt of formula II

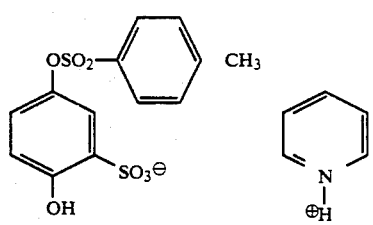

(II)

which in its turn has been obtained by tosylation in a pyridine medium of the diethylamine salt of 2,5-dihydroxybenzenesulphonic acid, of formula III, also known as ethamsylate.

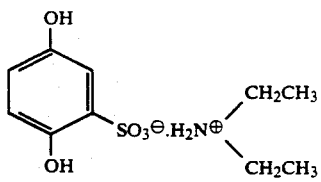

(III)

The same process is described in identical terms in the American patents U.S. Pat. No. 3,954,767 and U.S. Pat. No. 4,115,648, also in the name of Lab. del Dr. Esteve, S. A.

This process enables the desired product to be obtained, but has considerable disadvantages for its industrial application.

In the first place, the use of pyridine as a reaction medium always has significant drawbacks, such as its toxicity, high cost and difficulty of recovery.

Moreover, it is difficult to displace the pyridine completely from the salt of formula II to obtain a piperazine sultosylate of the purity required for its use in a pharmaceutical speciality.

DESCRIPTION OF THE INVENTION

According to the process described in the present invention, the compound I is manufactured by means of a three-stage process from the diethylamine salt of 2,5-dihydroxybenzenesulphonic acid of the formula III or from the ammonium salt of the same acid of the formula IV

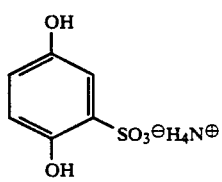

(IV)

In the first stage, either of the two alternative starting materials is tosylated stoichiometrically with p-toluene sulphonyl chloride in an ammoniacal medium, to lead in both cases to the production of the ammonium salt of 2,5-dihydroxybenzenesulphonic acid monotosylate of formula V

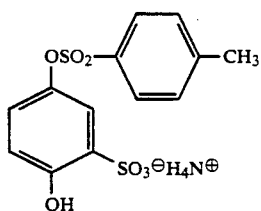

(V)

The monotosylated ammonium salt thereby obtained is treated in an aqueous medium with piperazine, and the disalt of formula VI

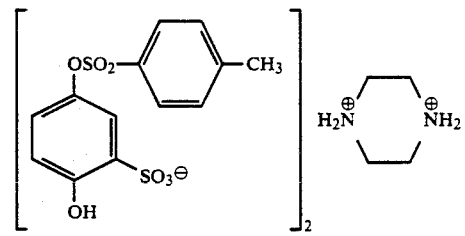

(VI)

is isolated in an acid medium.

In the third stage, the disalt of the formula VI is treated with an excess of piperazine in an aqueous-alcoholic medium to obtain finally the desired product of formula I, which is isolated by filtration.

DESCRIPTION OF EXAMPLES OF EMBODIMENT

To facilitate the understanding of the process which is the subject of the present invention, examples of the process are provided, but should not be considered to be limiting.

EXAMPLE 1

Preparation of the ammonium salt of 2,5-dihydroxybenzenesulphonic acid monotosylate 150 g (0.787 mol) of tosyl chloride, dissolved beforehand in 200 ml of dimethylformamide, are added slowly to a solution of 214 g (0.813 mol) of the diethylamine salt of 2,5-dihydroxybenzenesulphonic acid and 70 ml of 25% strength aqueous ammonia in 300 ml of water cooled to 0° C.

When the addition is complete, the mixture is maintained for two hours at 0–5° C., during which a white solid precipitates. The pH is adjusted to 4 with hydrochloric acid and the product is filtered off and washed with water.

271 g (92%) of a white solid, m.p. 145–147° C., are thereby obtained.

IR (KBr): characteristic bands at 3200, 3100, 1665, 1430, 1370, 1185 and 1025 cm$^{-1}$.

EXAMPLE 2

Preparation of the ammonium salt of 2,5-dihydroxybenzenesulphonic acid monotosylate Working in an identical manner to that described in Example 1, but using 168 g (0.811 mol) of the ammonium salt of 2,5-dihydroxybenzenesulphonic acid, 256 g (87%) of a white solid, whose analytical characteristics are identical to those of the product obtained in Example 1, are finally obtained.

EXAMPLE 3

Preparation of the piperazine double salt of 2,5-dihydroxybenzenesulphonic acid monotosylate 207 g (0.571 mol) of the ammonium salt of 2,5-dihydroxybenzenesulphonic acid monotosylate are dissolved in 350 ml of water at 70°–80° C. To the hot solution, 24.1 g (0.279 mol) of piperazine are added, the mixture is stirred for 15 minutes, and at 50–55° C. hydrochloric acid is added to pH 1.

The mixture is cooled to 0° C. and the product is filtered off and washed with water, 190 g (86%) of a white solid, m.p. 246–248° C., being obtained.

IR (KBr): characteristic bands at 3500, 3380, 3240, 2820, 2780, 2740, 1590, 1430, 1170 and 1020 cm$^{-1}$.

EXAMPLE 4

Preparation of the piperazine salt of 2,5-dihydroxybenzenesulphonic acid monotosylate (piperazine sultosylate)

190 g (0.245 mol) of the piperazine double salt obtained according to the preceding example are added to a solution at 70° C. of 31.6 g (0.367 mol) of piperazine in 340 ml of ethanol.

The mixture is heated to 80–85° C. and about 20 ml of water are added until total dissolution is obtained. The mixture is cooled slowly to 0° C. and maintained for one hour at this temperature, the product is filtered off, washed with ethanol and dried, 192 g (91%) of a crystalline white solid, m.p. 168–170° C., being obtained.

IR (KBr): characteristic bands at 3340, 3060, 2860, 2780, 2500, 1600, 1440, 1375, 1240, 1200, 1040 and 925 cm$^{-1}$.

We claim:

1. A process for preparing a piperazine salt of 2,5 dihydroxybenzenesulphonic acid monotosylate, of Formula I,

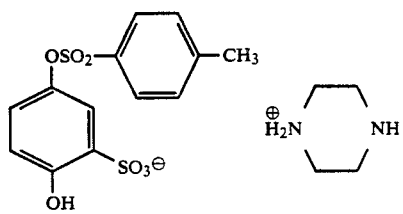

comprising:
1) tosylating either a diethylamine salt or an ammonium salt of 2,5-dihydroxybenzenesulphonic acid in aqueous ammonia to produce an ammonium salt of 2,5-dihydroxybenzenesulphonic acid monotosylate;
2) mixing the ammonium salt of 2,5-dihydroxybenzene sulphonic acid monotosylate with piperazine in an aqueous medium to obtain a piperazine disalt;
3) isolating the corresponding piperazine disalt;
4) treating the piperazine disalt with an excess of piperazine in an aqueous-alcohol medium and
5) isolating the product of Formula I.

2. A process according to claim 1 wherein stoichiometric molar quantities of tosyl chloride or p-toluene sulphonyl chloride and either the diethylamine salt or the ammonium salt of 2,5-dihydroxybenzene sulphonic acid is used to obtain the ammonium salt of 2,5-dihydroxybenzenesulphonic acid monotosylate.

3. A process according to claim 2 wherein the alcohol used in the aqueous-alcohol medium is selected from the group consisting of methanol, ethanol and isopropanol.

* * * * *